United States Patent [19]
Kallok

[11] Patent Number: 5,324,309
[45] Date of Patent: Jun. 28, 1994

[54] OVERLAPPING PULSE CARDIOVERSION OR DEFIBRILLATION

[75] Inventor: Michael J. Kallok, New Brighton, Minn.

[73] Assignee: Medtronic, Inc., Minneapolis, Minn.

[21] Appl. No.: 951,622

[22] Filed: Sep. 25, 1992

[51] Int. Cl.$^5$ ............................................. A61N 1/39
[52] U.S. Cl. ...................................................... 607/5
[58] Field of Search ...................... 128/419 D, 420 A; 607/5, 7, 66, 67, 68, 70, 72, 4

[56] References Cited

U.S. PATENT DOCUMENTS

| | | | |
|---|---|---|---|
| 3,605,754 | 9/1971 | Jaros et al. | 128/419 D |
| 4,407,288 | 10/1983 | Langer et al. | 128/419 PG |
| 4,708,145 | 11/1987 | Tacker, Jr. et al. | 128/419 D |
| 4,727,877 | 3/1988 | Kallok | 128/419 D |
| 4,800,883 | 1/1989 | Winstrom | 128/419 D |
| 4,830,006 | 5/1989 | Haluska et al. | 128/419 PG |
| 4,850,357 | 7/1989 | Bach, Jr. | 128/419 D |
| 4,949,719 | 8/1990 | Pless et al. | 128/419 D |
| 4,953,551 | 9/1990 | Mehra et al. | 128/419 D |
| 5,163,427 | 11/1992 | Keimel | 128/419 D |

FOREIGN PATENT DOCUMENTS 7401383  1/1974  France ........................... A61N 1/36

OTHER PUBLICATIONS

Kerber, et al., "Overlapping Sequential Pulses: A New Wave Form for Transthoracic Defibrillation" Abstract, Circulation Supplement, Oct. 1991.

Primary Examiner—Lee S. Cohen
Assistant Examiner—Jeffrey R. Jastrzab
Attorney, Agent, or Firm—Reed A. Duthler; Harold R. Patton

[57] ABSTRACT

A method and apparatus for cardioversion and defibrillation. The apparatus is provided with two pairs of cardioversion or defibrillation electrodes, and delivers pulses sequentially between said first and second pairs of electrodes, such that the first pulse overlaps the second pulse for a time interval of at least about one millisecond. During the overlap time of the first and second pulses, a defibrillation pulse vector intermediate that defined by the two electrode pairs individually is provided.

12 Claims, 6 Drawing Sheets

OVERLAPPING PULSE CARDIOVERSION OR DEFIBRILLATION

BACKGROUND OF THE INVENTION

This invention relates generally to the field of electrical stimulators, and more particularly to cardioverters and defibrillators.

The earliest cardioverters and defibrillators generated either a single burst of alternating current or a single pulse for application to the heart to cause cardioversion or defibrillation. However, the use of multiple pulses to accomplish cardioversion or defibrillation has also been extensively researched. For example, U.S. Pat. No. 3,605,754 issued to Jaros, et al., on Sep. 20, 1971 discloses an early double pulse heart defibrillator employing two capacitors which are successively discharged between a single pair of electrodes. Later, the use of multiple electrode systems, in which defibrillation pulses were delivered successively between different electrode pairs chosen from among the electrodes available was suggested. For example, U.S. Pat. No. 4,727,877 issued to Kallok on Mar. 1, 1988 and U.S. Pat. No. 4,708,145 issued to Tacker, Jr. et al., on Nov. 24, 1987, both disclose a variety of implantable, multiple electrode systems adapted for use in conjunction with a sequential pulse defibrillator, in which pulses are applied sequentially to different pairs of electrodes.

French Patent Application No. 74/01383, Publication No. 2,257,312 by Zacouto discloses internal and external sequential pulse defibrillators employing multiple electrodes arranged in and around the heart. In the Zacouto application, A.C. defibrillation pulses are sequentially delivered such that each successively activated electrode pair defines a pulse vector, and such that the pulse vectors scan in a rotational fashion through the heart tissue. Pulses are delivered immediately following one another, or may overlap one another for some unspecified period. More recently, delivery of pulses simultaneously between multiple electrode pairs has been extensively pursued. For example, U.S. Pat. No. 4,953,551, issued to Mehra et al., on Sep. 4, 1990, discloses simultaneous delivery of pulses between the superior vena cava and the right ventricle and between the right ventricle and a subcutaneous electrode.

The ability to deliver sequential and simultaneous pulses to different pairs of electrodes is incorporated in the Medtronic implantable pacemaker/cardioverter/defibrillators presently in clinical evaluation in the United States. The pulse generation circuitry in these devices corresponds to that disclosed in allowed U.S. patent application Ser. No. 07/612,758 for an Apparatus for Delivering Single and Multiple Cardioversion and Defibrillation Pulses, filed Nov. 14, 1990 by Keimel, now U.S. Pat. No. 5,163,427 incorporated herein by reference in its entirety. In these devices, two capacitor banks are provided which are simultaneously charged and then successfully or simultaneously discharged between different pairs of electrodes.

It has also been proposed to apply biphasic pulses to individual electrode pairs, in which a positive pulse is followed by a negative pulse, typically having an initial amplitude equal to the trailing edge amplitude of the first pulse, but at a reversed polarity. Apparatus for delivering such biphasic pulses are disclosed in U.S. Pat. No. 4,850,357 issued to Bach, Jr. on Jul. 25, 1989, U.S. Pat. No. 4,953,551 issued to Mehra et al., on Sep. 4, 1990, and in U.S. Pat. No. 4,800,883 issued Jan. 31, 1989 to Winstrom, all of Which are incorporated herein by reference in their entireties. In all three references, it is proposed to deliver the biphasic pulse by the use of a single capacitor or a capacitor bank in which capacitors are charged and discharged together to deliver the biphasic pulse.

The electrode configurations and pulse regimens described in the above-cited patents have all been tested clinically, and all, in at least some patients, provide a benefit as compared to a monophasic pulse regimen delivered between a single pair of electrodes. Some researchers have found that the use of a biphasic pulse regimen provides a reduction in the energy required to defibrillate, when the biphasic pulse is used in either a two electrode system or a three electrode system as proposed in Mehra, with two electrodes tied together during delivery of the biphasic pulse. Some researchers have also found that sequential delivery of monophasic pulses between two different 5 electrode pairs, as described in the above-cited Kallok and Tacker Jr., references provides a reduction in energy thresholds as compared to a single delivered monophasic pulse. Nonetheless, there is still a substantial desire for further reductions in overall energy thresholds associated with defibrillation, in the context of implantable defibrillators. Reduction of energy threshold allows for the use of smaller batteries or provides for increased longevity in these devices, and is an area of on-going research activities, both within the medical community and by manufacturers of implantable cardioverters and defibrillators.

SUMMARY OF THE INVENTION

The present invention is directed toward providing an incremental reduction in energy threshold in systems employing multiple pulses delivered between different electrode pairs. The present invention, rather than delivering pulses of equal amplitude, successively or simultaneously, between different electrode pairs delivers pulses which have sequential initiation and termination times, but which overlap one another to a significant degree to effectively define an additional pulse vector intermediate to the pulse vectors defined by the individual electrodes. The degree of overlap and the relative durations of the overlapped and non-overlapped portions of the pulses and the relative amplitudes of the pulses may be adjusted as desired to control the relative amounts of energy delivered to the heart tissue along the defined pulse vectors. In one illustrated embodiment, two equal duration 10 pulses are delivered with a fifty percent overlap, such that approximately twice the energy is delivered along the pulse vector defined during the overlapped portions of the pulses as during the individual non-overlapped portions. While the relative amount of overlap may be adjusted, it is believed that the duration of the overlapped portion of the pulses and the duration of the non-overlapped portion of at least one and preferably both of the pulses should be at least about one or two milliseconds in order to get the benefit from the pulse vector defined during both the overlapped and non-overlapped portions.

DETAILED DESCRIPTION OF THE PREFERRED EMBODIMENTS

Figure 1:
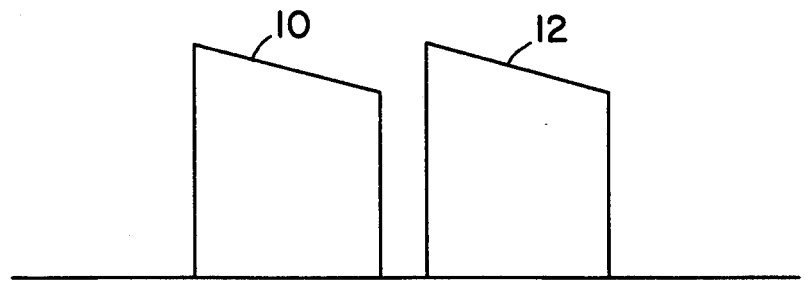
FIG. 1 is an illustration of prior art sequentially applied defibrillation pulses.

FIG. 1 illustrates the delivered pulses of a prior art sequential pulse defibrillation system. As illustrated, the wave form comprises two successive truncated exponential, capacitive discharge wave forms 10 and 12. As described in the above-cited Jaros, et al., patent, these pulses are generally delivered using separate capacitor banks which are simultaneously charged and successively discharged. As described in the above-cited Tacker, et al., and Kallok, patents, in the context of multiple pulse, multiple electrode systems, the first pulse 10 is typically delivered between a first electrode pair and the second pulse 12 is typically delivered between a second electrode pair. The first and second electrode pairs may or may not have an electrode in common.

Figure 2:
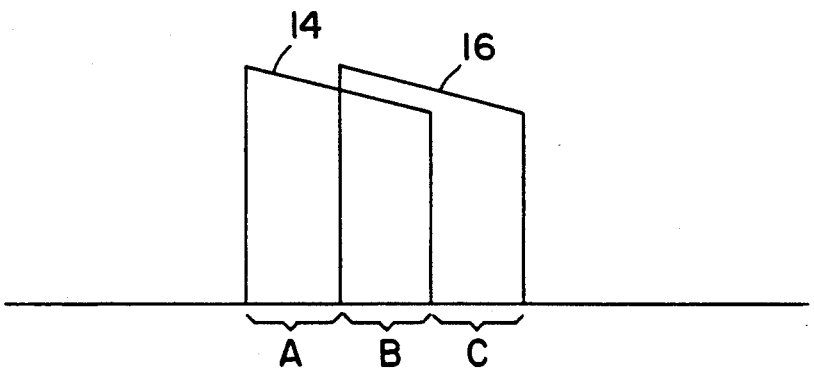
FIG. 2 is an illustration of overlapping defibrillation pulses according to the present invention.

FIG. 2 is an illustration of the multiple pulse output of the present invention. As illustrated, a first pulse 14 is delivered by discharging a first capacitor bank and the second pulse 16 is delivered by discharging a second capacitor bank. The first pulse 14 is delivered to a first pair of electrodes and the second pulse 16 is delivered to a second pair of electrodes. As illustrated, pulse 14 and pulse 16 overlap one another to a significant degree, defining three time intervals A, B and C. Intervals A and C comprise the non-overlapping periods of the pulses. Interval B comprises the overlapping portions of the pulses. As discussed above, different pulse vectors are defined during each of intervals A, B and C.

As illustrated, the amplitudes of pulses 14 and 16 are equal. However, pulses of different amplitude may be employed to provide more control of the relative amounts of energy delivered along each pulse vector. Similarly, while the durations of pulses 14 and 16 as illustrated are equal and the durations of intervals A, B and C as illustrated are equal (each being 50% of the duration of pulses 14 and 16), these time intervals may also be varied to provide increased control of the energy delivered along each pulse vector. However, in order to get the benefit of a pulse delivered along a defined pulse vector, the associated time interval A, B or C should have a duration of at least about 1 or 2ms.

In experiments verifying the operability of the sequential overlapping pulse invention, the inventor typically employed pulses of five milliseconds each, with an overlap of two and one-half milliseconds each. In the specific implantable electrode configurations tested, the inventor found that over a group of test animals, sequential pulse systems and overlapping pulse systems exhibited similar energy thresholds, however, some animals had displayed lower energy thresholds when provided with an overlapping pulse regimen than with a sequential pulse regimen. Moreover, testing on versions of the invention employing external electrodes, as described in an abstract entitled "Overlapping Sequential Pulses: A New Waveform for Transthoracic Defibrillation", by Kerber, Kallok, Birkett, Fox-Eastham, Yoerger and Kieso, published in the Oct., 1991 Circulation Supplement, the use of overlapping sequential pulses was found to provide a benefit in reducing overall energy thresholds. It should thus be understood that the benefit of the present invention may present itself on an individualized basis, as compared to prior simultaneous or sequential defibrillation systems.

The present invention also provides the valuable ability to adjust and redefine defibrillation pulse vectors, after implantation or installation of an electrode system, by defining new pulse vectors as a result of the polarity, duration, amplitude and degree of overlap of two sequentially delivered pulses. The ability to define new defibrillation pulse vectors after implant, in and of itself is believed to be of substantial benefit, and is not provided in the same fashion by prior sequential and simultaneous pulse delivery systems. Moreover, the overlapping pulse system provides for the ability to deliver a sweeping or scanning pulse train with a greater number of defined defibrillation pulse vectors than would be possible by delivery of sequential pulses.

Figure 3:
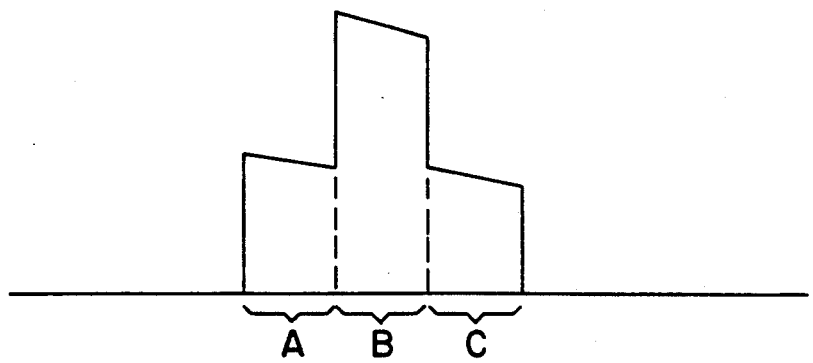
FIG. 3 illustrates the current levels delivered during sequential overlapping pulses according to the present invention.

FIG. 3 illustrates the combined current wave-form during intervals A, B and C. As illustrated, the current amplitude during interval B is greater than during intervals A and C. The degree of current amplitude difference is dependent on the relative impedances of the electrodes employed to deliver the two pulses. The current delivered during C is the instantaneous sum of currents A and B at each instant of overlap.

Figure 4:
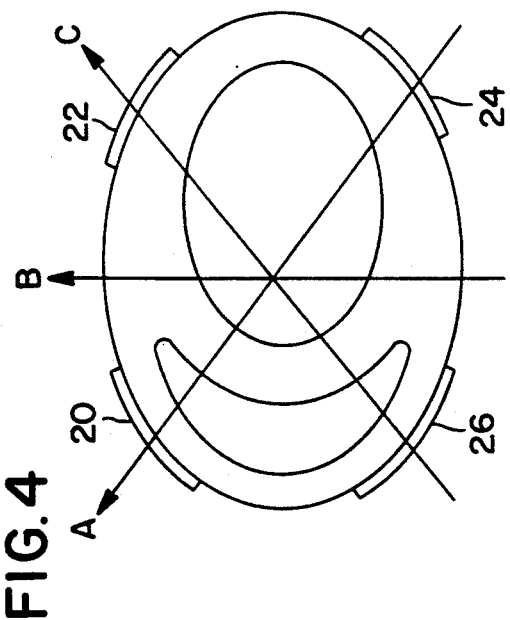

FIG. 4 is a cross-section through the ventricle of a human heart, illustrating an electrode system comprising four electrodes 20, 22, 24 and 26. FIG. 4 illustrates a first set of pulse vectors, labeled A, B and C according to the time interval during which the vectors are defined. These vectors are defined by delivering a pulse between electrode 22 and 26, with electrode 26 coupled to the positive terminal of a first output capacitor bank of a defibrillator and a pulse between electrodes 20 and 24 with electrode 24 coupled to the positive terminal of a second output capacitor bank of a defibrillator, with an overlap period B. The pulse vector illustrated as occurring during interval B as illustrated should not be interpreted as suggesting that electrical current flows only along the directional line illustrating the pulse vector. As a practical matter, during the overlap period, field density and current flow will be greatest in the areas between oppositely charged electrodes, that is between electrodes 20 and 26 and between electrodes 22 and 24, with a net pulse vector as illustrated during interval B.

Figure 5:
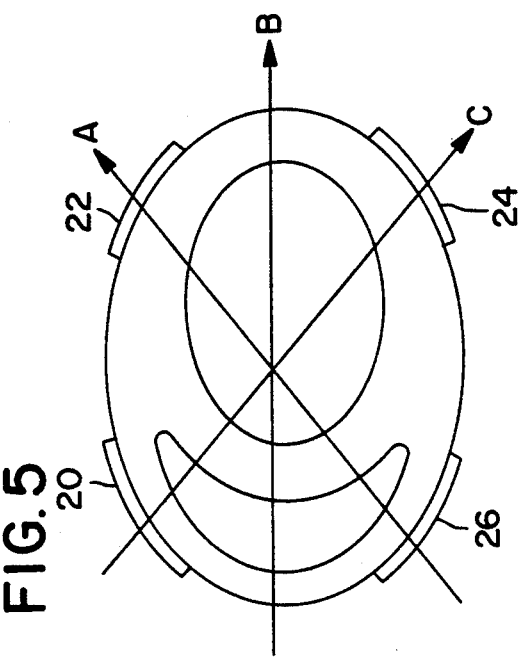
FIGS. 4, 5, 6 and 7 illustrate multiple electrode systems applied to the ventricles of the heart, and the pulse vectors defined during delivery of overlapping pulses according to the present invention.

FIG. 5 illustrates the same electrode system, with polarity reversed with regard to electrodes 20 and 24. In this system, a first pulse is delivered between electrodes 22 and 26 with electrode 26 coupled to the positive terminal of the first output capacitor bank and a second, overlapping pulse delivered between electrodes 20 and 24 with electrode 20 coupled to the positive terminal of the second output capacitor bank. In this case, the pulse vector during interval B is rotated 90° from the direction of the pulse vector defined during the overlap period B as illustrated in FIG. 4. FIGS. 4 and 5 thus illustrate how reversal polarity of a single electrode pair can result in definition of different pulse vectors during the overlap period. Thus, in a system in which electrode polarities are individually selectable, the flexibility of the overlapping pulse regimen is substantially enhanced.

Figure 6:
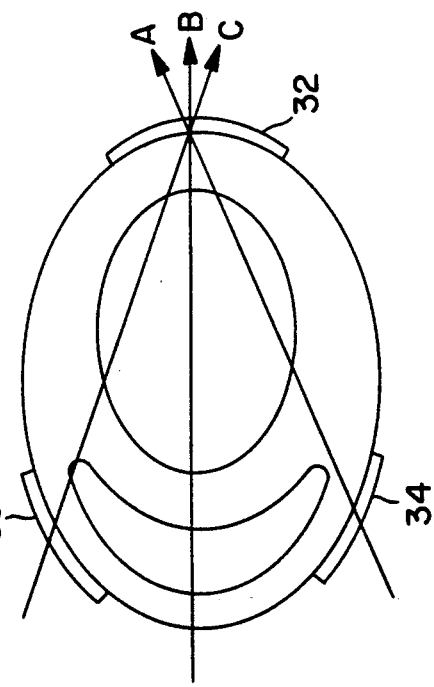

FIG. 6 illustrates one electrode configuration tested by the inventors, which comprised three electrodes. One electrode 30, was located on the posterior right ventricle, one electrode 32, was located on the left ventricular free wall, and one electrode 34, was located on the anterior right ventricle. The inventors applied a first pulse between the anterior right ventricular electrode 34 and the left ventricular electrode 32 and thereafter applied a second pulse between the posterior right ventricular electrode 30 and the left ventricular electrode 32. Both sequential and overlapped pulses were tested using this configuration. In general, the inventors found the over-all energy efficiency of the overlapping pulse regimen to be similar to the sequential pulse regimen. However, some individual dogs tested showed lower energy thresholds with the overlapping pulse regimen.

Figure 7:
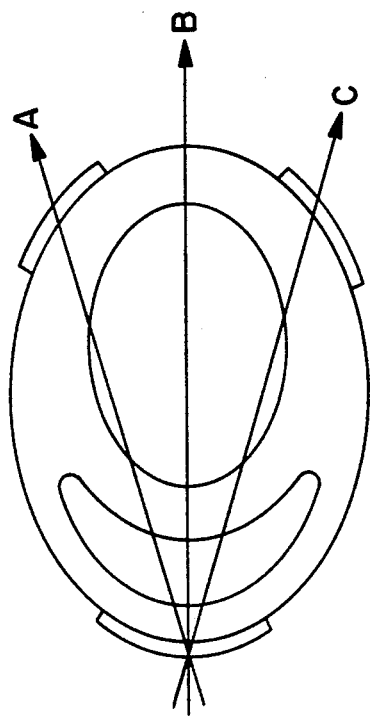

FIG. 7 illustrates an alternative arrangement of the three electrode system illustrated in FIG. 6, in which the electrodes 30, 32 and 34 are slightly rearranged such that electrodes 32 and 34 are located adjacent the left ventricle and electrode 30 is located adjacent the right ventricle. Pulse vectors during time intervals A, B and C are illustrated, resulting from delivery of a first pulse between electrodes 30 and 32 and a second, overlapping pulse delivered between electrodes 30 and 34. In this case, the pulse vectors scan through the left ventricle.

Figure 8B:
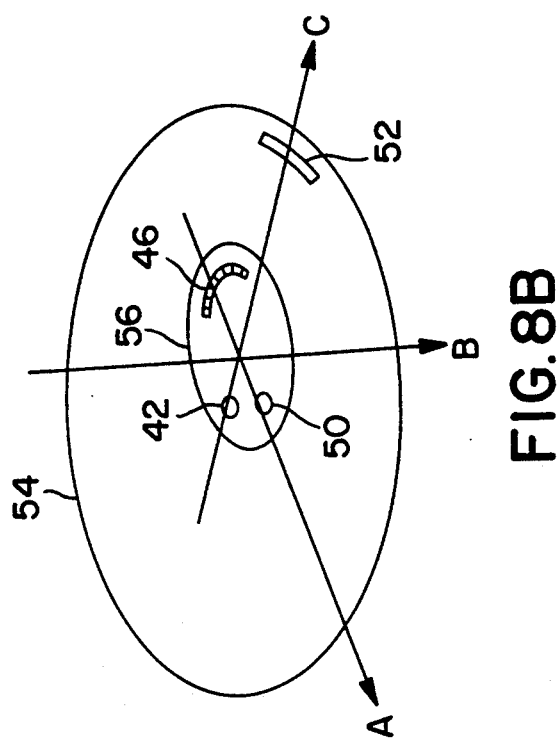
FIGS. 8a, 8b, 9a, 9b, 10a and 10b illustrate multiple electrode systems including at least three electrodes taken from the set of electrodes comprising a superior vena cava electrode, a coronary sinus electrode, a right ventricular electrode and a subcutaneous electrode, illustrating the pulse vectors defined during delivery of overlapping pulses according to the present invention.
Figure 8A:
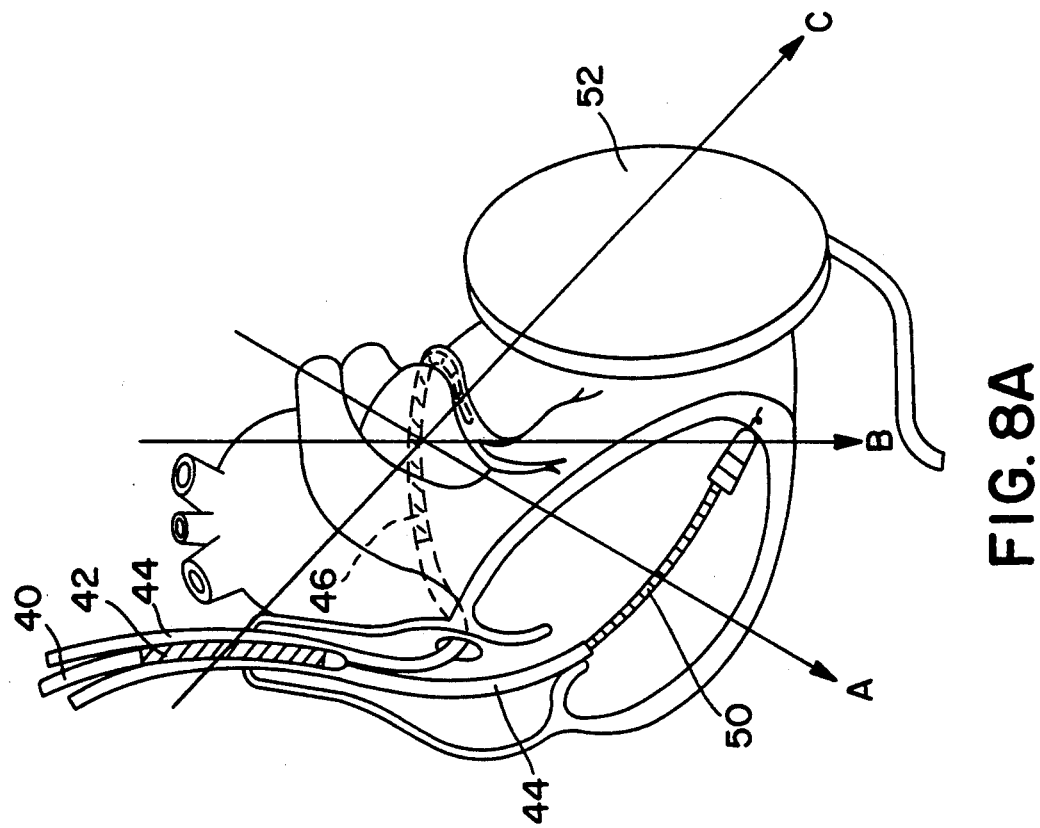

FIGS. 8a and 8b illustrate a four electrode transvenous/subcutaneous electrode system including a first lead 48 carrying an electrode 50 located in the right ventricle, a second lead 40 carrying an electrode 42 located in the superior vena cava, a third lead 44 carrying an elongated electrode 46 located in the coronary sinus and great cardiac vein and a subcutaneous patch electrode 52. FIG. 8a is cutaway view of the heart. FIG. 8b is a cross-sectional view through the thorax 54 an the heart 56. FIG. 8a and 8b illustrate at A, B, and C the sequentially defined pulse vectors associated with an overlapping pulse regimen including a first pulse delivered between electrode 46 and electrode 50 and a second pulse delivered between electrode 44 and 52. This pulse regimen was also tested by the inventor to determine operability. As in the case of the electrode set illustrated in FIG. 6, comparable energy thresholds to sequential pulses were obtained, with some experimental animals displaying lower energy thresholds using the overlapping pulse regimen. As illustrated, by arranging the electrodes 42, 50, 46 and 52 in a three dimensional network around the heart, a three dimensional set of pulse vectors is described, such that the pulse vectors scan in three dimensional space, through the tissue of the heart.

Figure 9B:
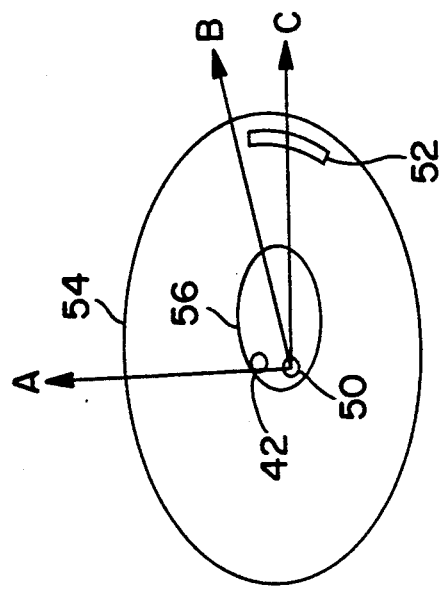
Figure 9A:
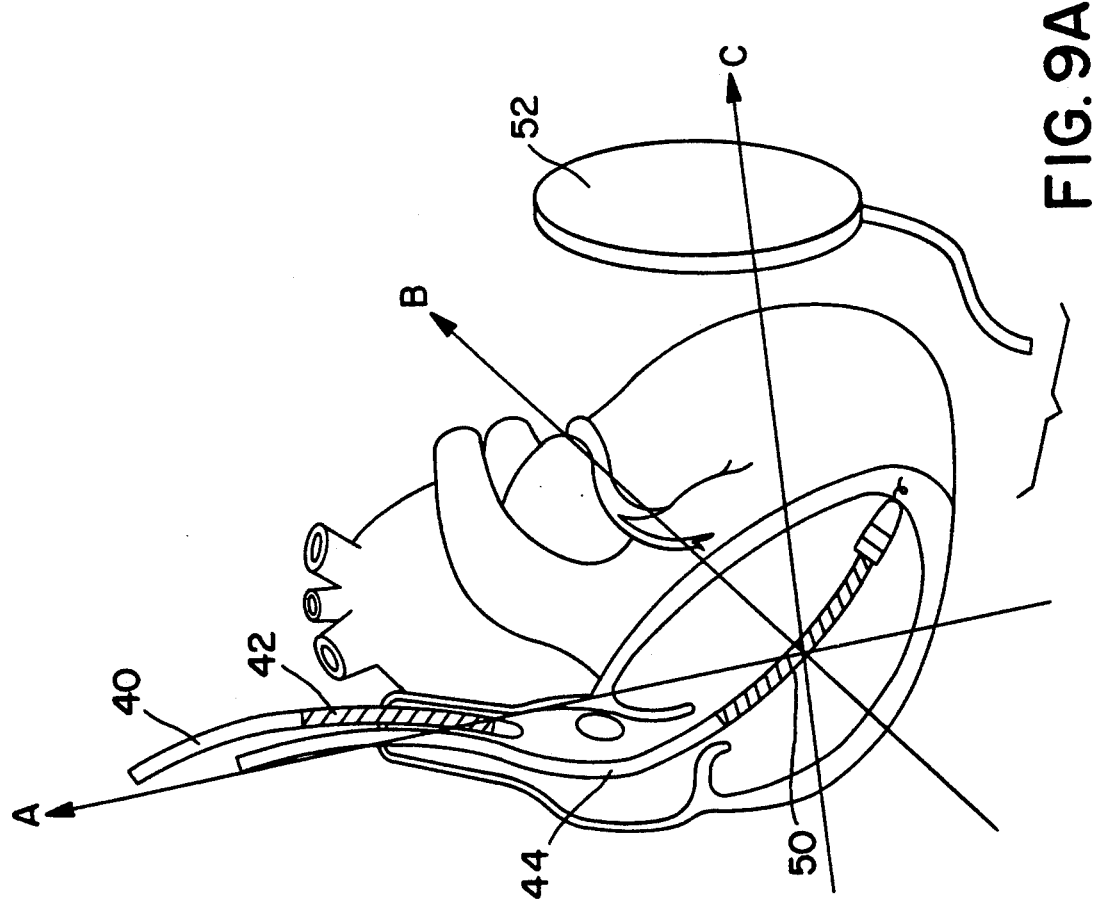

FIGS. 9a and 9b illustrate the same electrode system illustrated in FIGS. 8a and 8b, with the deletion of electrode 46 and lead 44. These drawings illustrate a set of pulse vectors occurring during intervals A, B, and C associated with an overlapping pulse regimen including a first pulse delivered between electrodes 50 and 42 and a second, overlapping pulse is delivered between electrodes 50 and 52. Like the overlapping pulse regimen illustrated in FIGS. 8a and 8b, a three dimensional scan of the pulse vector is provided.

Figure 10B:
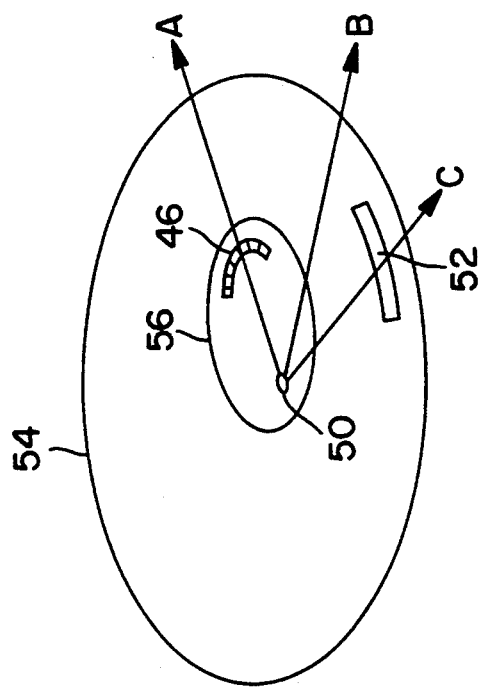
Figure 10A:
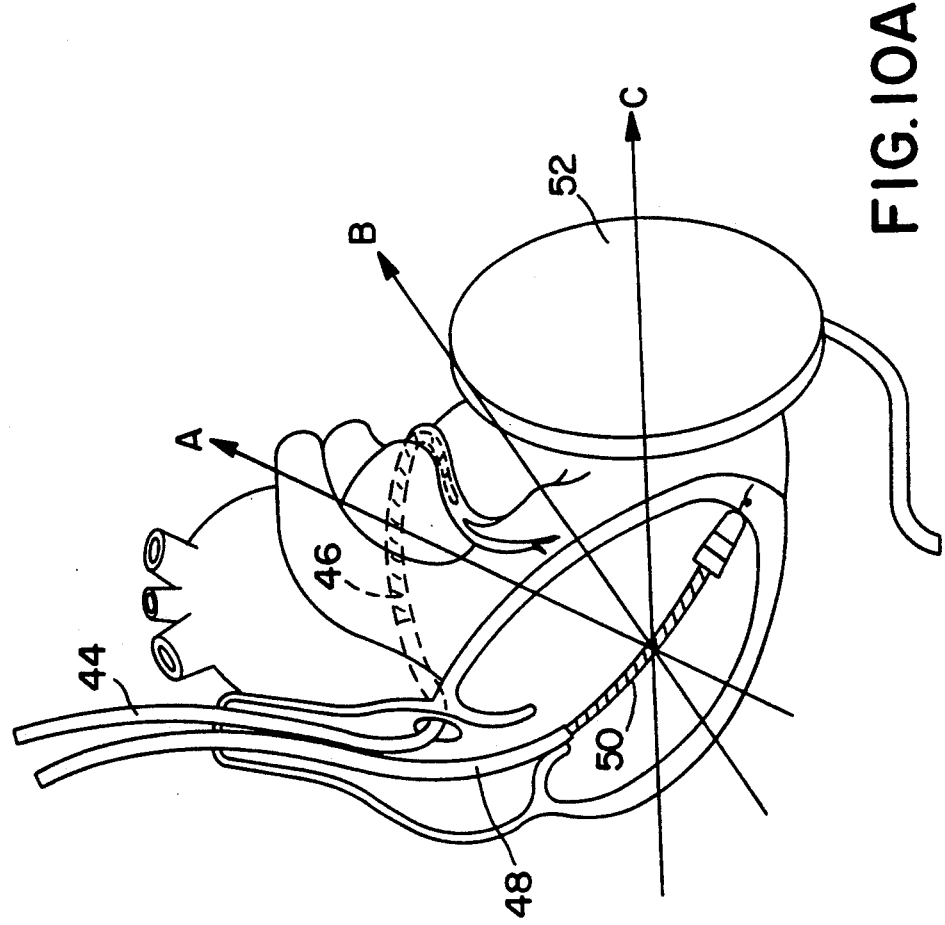

FIGS. 10a and 10b similarly illustrate an electrode system which is a subset of electrodes illustrated in FIGS. 8a and 8b, this time, with lead 40 and electrode 42 removed. In this case, a set of three defibrillation pulse vectors during intervals A, B and C is illustrated associated with an overlapping pulse regimen comprising delivery of a first pulse between electrodes 50 and 46 and a second, overlapping pulse delivered between electrodes 50 and 52 such that electrode 52 is coupled to the positive terminal of the capacitor bank. As illustrated in FIGS. 10a and 10b, a three dimensional scan of the pulse vectors is similarly provided.

From an examination of FIGS. 8a, 8b, 9a, 9b, 10a and 10b, it can be seen that provision of pulse overlap substantially adds to the available pulse vectors which may be delivered using endocardial and subcutaneous defibrillation leads of the types presently available for use in conjunction with implantable pacemaker/cardioverter/defibrillators, even in systems employing only three such electrodes. By specifying the electrodes employed to deliver the first and second pulses and their polarities, along with the overlap time and the relative charge levels in the output capacitors discharged during the first and second pulses, an enormous variety of sets of scanned pulse vectors arrayed in three dimensional space can be selected in order to optimize the pulse delivery regimen to particularly suit the patient in whom the device is implanted.

Figure 11:
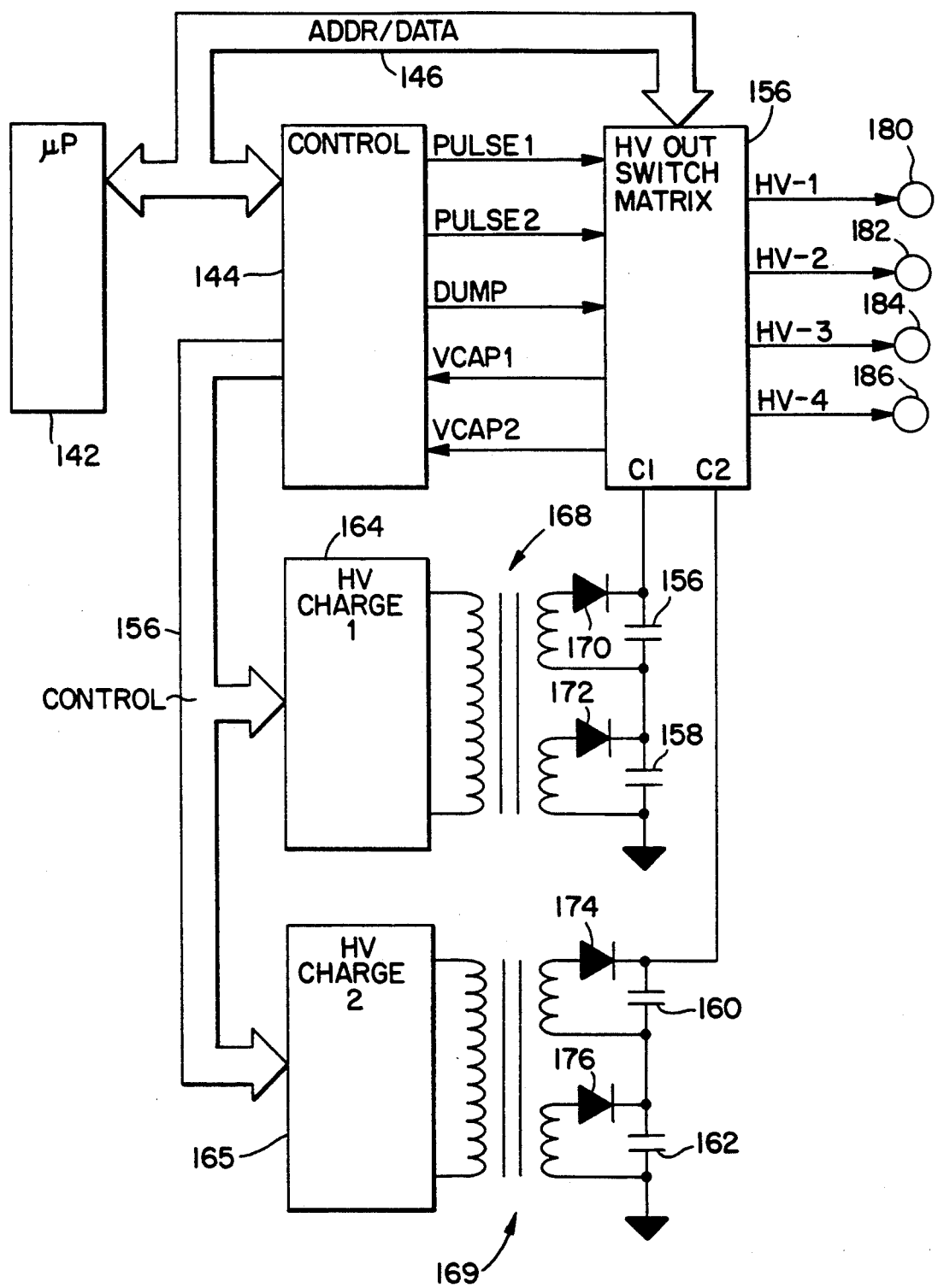
FIG. 11 is a block, functional diagram of a multiple pulse defibrillator of the type that could be employed to practice the present invention.

FIG. 11 illustrates a proposed embodiment of a multiple pulse defibrillator embodying present invention. All of the components illustrated are readily available and well known to the art, and therefore are illustrated in functional form only. FIG. 11 illustrates only those portions of the device associated with control of pulse duration, electrode selection and pulse duration and their interconnection to a microprocessor of the type typically employed to control the operations of pacemaker/cardioverter/defibrillators of the type in which the invention may usefully be employed.

Output capacitors 156, 158, 160 and 162 form two capacitor banks. They are simultaneously charged by high voltage charging circuitry 164, 165 by means of high voltage step-up transformers 168 and 169 under control of control circuitry 144 via control bus 166. Charging is initiated in response to detection of a tachyarrhythmia by the microprocessor, as described in the above-cited Keimel application. Diodes 170, 172, 174 and 176 rectify the AC signals provided by the transformers 168 and 169 to provide a net DC charge on the capacitors. The high voltage charging circuitry 164, 165 controlling the delivery of electrical current to the step-up transformers may correspond to that disclosed in U.S. Pat. No. 4,548,209, issued to Wielders et al, incorporated herein by reference in its entirety.

The voltage on the first capacitor bank 156, 158 is provided to control circuitry 144 on VCAP 1 line 154. The voltage on the second capacitor bank 160, 162 is provided to control circuitry 144 on VCAP 2 line 155. Charging continues until the voltages on lines 154 and 155 reach preset voltage thresholds defined by microprocessor 142. The voltage thresholds for the two capacitor banks may be the same or may differ.

Four output electrodes are illustrated, including electrode 180, coupled to output line HV-1, electrode 182 coupled to output line HV-2, electrode 184 coupled to output line HV-3 and electrode 186 coupled to output line HV-4. For example, electrodes 180, 182, 184 and 186 may correspond to electrodes 42, 52, 46 and 50 in FIG. 8a or to electrodes 24, 20, 26 and 22 as illustrated in FIG. 4. Control of the timing of the pulses is provided by control circuitry 144, which sequentially provides overlapping logic signals on PULSE 1 line 148 and PULSE 2 line 150. The timing and durations of these logic signals correspond to the desired pulse durations. Selection of the electrodes employed to deliver the pulses, and of the polarity of the pulses is accomplished by microprocessor 142 via output switch matrix 156. Interconnection of the capacitor banks and the electrodes is provided by means of a sets of electronic switches within switch matrix 156 which are selected by microprocessor 142 via address/data bus 146 and Which couple the positive terminal of the first capacitor bank 156, 158 to a first selected electrode or electrodes during the first pulse, couple the positive terminal of the second capacitor bank 160, 162 to a second selected electrode or electrodes during the second pulse, couple the negative terminal of the capacitor bank 156, 158 to a third selected electrode or electrodes during the first pulse and couple the negative terminal of the capacitor bank 160, 162 to a fourth selected electrode or electrodes during the second pulse.

The switches employed to couple the positive terminals of the capacitor banks to the electrodes may correspond to the triac switches disclosed in the above-cited Keimel application, which are correspondingly used to connect to the positive side of the capacitor banks therein to the selected electrodes. Alternatively, FET switches as disclosed in the above-cited Winstrom et al patent may be employed if overall energy level demands are sufficiently low. SCR switches as described in the above-cited Mehra, et al., and Bach, et al., patents might also be employed. The electronic switches employed to couple the negative terminals of the capacitor banks to the electrodes may be, for example, FET switches as described in the above-cited Winstrom, et al., patent or SCR switches as described in the above-cited Mehra, et al., and Bach Jr., patents.

The circuitry illustrated in FIG. 11 may be readily incorporated into an implantable pacemaker/cardioverter/defibrillator, particularly a device similar to those currently in clinical evaluation by Medtronic, Inc. Alternatively, the device may similarly be practiced in the context of implantable pacemaker/cardioverter/defibrillators as disclosed in U.S. Pat. No. 4,407,288, issued to Langer, et al., U.S. Pat. No. 4,830,006, issued to Haluska, et al. or U.S. Patent No. 4,949,719, issued to Pless et al., all of which are incorporated herein by reference in their entireties.

While the disclosed embodiment is illustrated in a form adapted for inclusion in a microprocessor based implantable pacemaker/cardioverter/defibrillator, the invention may also usefully be practiced in defibrillators and cardioverters employing other circuit architecture including full custom digital logic or circuitry constructed of discreet, commercially available analog and digital components, so long as the essential functions and operations are preserved. As such, the above disclosure should be considered exemplary, rather than limiting with regard to the claims that follows.

In conjunction with the above specification, I claim:

1. Apparatus for cardiac cardioversion or defibrillation, comprising:
   a first pair of cardioversion or defibrillation electrodes;
   a second pair of cardioversion or defibrillation electrodes;
   a capacitor mean for storing charge comprising one or more capacitors and having positive and negative output terminals;
   means for sequentially coupling said positive and negative output terminals of said capacitor means to said first electrode pair for a first time interval to deliver a first cardioversion or defibrillation pulse and to said second electrode pair for a second time interval to deliver a second cardioversion or defibrillation pulse, said first and second time intervals overlapping one another such that during an overlap time interval of at least about one millisecond both said first and second pulses are being delivered and such that during a non-overlap interval of at least about one millisecond only one of said first and second pulses is being delivered.

2. Apparatus according to claim 1 wherein said coupling means comprises means for sequentially coupling said positive and negative output terminals of said capacitor bank to said first electrode pair for a first time interval to deliver a first cardioversion or defibrillation pulse and to said second electrode pair for a second time interval to deliver a second cardioversion or defibrillation pulse, said first and second time intervals overlapping one another such that during an overlap time interval of at least about one millisecond both said first and second pulses are being delivered and such that during two nonoverlap intervals of at least about one millisecond each only one of said first and second pulses is being delivered.

3. Apparatus according to claim 1 or claim 2 wherein said first and second electrode pairs comprise three electrodes and wherein one of said three electrodes comprises a common electrode, common to both said first and second electrode pairs.

4. Apparatus according to claim 1 or claim 2 wherein said coupling means comprises means for adjusting the duration of said overlap interval.

5. Apparatus according to claim 1 or claim 2 wherein said coupling means comprises means for adjusting the duration of said non-overlap interval.

6. Apparatus according to claim 1 or claim 2 wherein said capacitor means comprises first and second capacitor banks and wherein said coupling means comprises means for coupling said first capacitor bank to said first electrode pair during said first time interval and for coupling said second capacitor bank to said second electrode pair during said second time interval.

7. Method for cardiac cardioversion or defibrillation, comprising:
   applying a first pair of cardioversion or defibrillation electrodes to a patient's body;
   applying a second pair of cardioversion or defibrillation electrodes to said patient's body;
   coupling a capacitor means comprising one or more capacitors and having positive and negative output terminals to said first and second electrode pairs;
   sequentially coupling said positive and negative output terminals of said capacitor means said first electrode pair for a first time interval to deliver a first cardioversion or defibrillation pulse and to said second electrode pair for a second time interval to deliver a second cardioversion or defibrillation pulse, said first and second time intervals overlapping one another such that during an overlap time interval of at least about one millisecond both said first and second pulses are being delivered and such that during a nonoverlap interval of at least about one millisecond only one of said first and second pulses is being delivered.

8. A method according to claim 7 wherein said coupling step comprises sequentially coupling said positive and negative output terminals of said capacitor bank to said first electrode pair for a first time interval to deliver a first cardioversion or defibrillation pulse and to said second electrode pair for a second time interval to deliver a second cardioversion or defibrillation pulse, said first and second time intervals overlapping one another such that during an overlap time interval of at least about one millisecond both said first and second pulses are being delivered and such that during two non-overlap intervals of at least about one millisecond each only one of said first and second pulses is being delivered.

9. A method according to claim 7 or claim 8 wherein said step of applying said first and second electrode pairs comprises applying three electrodes and wherein one of said three electrodes comprises a common electrode, common to both said first and second electrode pairs.

10. A method according to claim 7 or claim 8 wherein said coupling step comprises adjusting the duration of said overlap interval.

11. A method according to claim 7 or claim 8 wherein said coupling step comprises adjusting the duration of said non-overlap interval.

12. A method according to claim 7 or claim 8 wherein said capacitor means comprises first and second capacitor banks and wherein said coupling step comprises coupling said first capacitor bank to said first electrode pair during said first time interval and for coupling said second capacitor bank to said second electrode pair during said second time interval.

* * * * *